US00PP25402P2

(12) United States Plant Patent
Sakazaki

(10) Patent No.: US PP25,402 P2
(45) Date of Patent: Mar. 31, 2015

(54) ***CALIBRACHOA* PLANT NAMED 'USCAL09301'**

(50) Latin Name: ***Calibrachoa* sp.**
Varietal Denomination: USCAL09301

(71) Applicant: Ushio Sakazaki, Hikone (JP)

(72) Inventor: Ushio Sakazaki, Hikone (JP)

(73) Assignee: Plant 21 LLC, Bonsall, CA (US)

( * ) Notice: Subject to any disclaimer, the term of this patent is extended or adjusted under 35 U.S.C. 154(b) by 147 days.

(21) Appl. No.: 13/815,883

(22) Filed: Mar. 15, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. A. Whealy

(57) ABSTRACT

A new and distinct cultivar of *Calibrachoa* plant named 'USCAL09301', characterized by its upright, outwardly spreading to trailing and mounding plant habit; freely branching habit; dense and bushy appearance; early and freely flowering habit; pale golden yellow-colored flowers with dark rusty red-colored venation and eye; and good garden performance.

1 Drawing Sheet

Botanical designation: *Calibrachoa* sp.
Cultivar denomination: 'USCAL09301'.

BACKGROUND OF THE INVENTION

The present invention relates to a new and distinct cultivar of *Calibrachoa* plant, botanically known as *Calibrachoa* sp. and hereinafter referred to by the name 'USCAL09301'.

The new *Calibrachoa* plant is a product of a planned breeding program conducted by the Inventor in Higashiomi, Shiga, Japan and Bonsall, Calif. The objective of the breeding program is to create new uniform and freely-branching *Calibrachoa* plants with unique and attractive flower coloration and good garden performance.

The new *Calibrachoa* plant originated from a cross-pollination made by the Inventor on May 8, 2010 in Higashiomi, Shiga, Japan of a proprietary seedling selection of *Calibrachoa* sp. identified as code name 10CJ04-03, not patented, as the female, or seed, parent with a proprietary seedling selection of *Calibrachoa* sp. identified as code name 10CJ70-02, not patented, as the male, or pollen, parent. The new *Calibrachoa* plant was discovered and selected by the Inventor as a single flowering plant within the progeny of the stated cross-pollination in a controlled environment in Bonsall, Calif. on May 13, 2011.

Asexual reproduction of the new *Calibrachoa* plant by terminal cuttings in a controlled environment in Bonsall, Calif. since May 14, 2011 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL09301'. These characteristics in combination distinguish 'USCAL09301' as a new and distinct *Calibrachoa* plant:

1. Upright, outwardly spreading to trailing and mounding plant habit.
2. Freely branching habit; dense and bushy appearance.
3. Early and freely flowering habit.
4. Pale golden yellow-colored flowers with dark rusty red-colored venation and eye.
5. Good garden performance.

The new *Calibrachoa* plant can be compared to plants of the female parent selection. Plants of the new *Calibrachoa* differ primarily from plants of the female parent selection in the following characteristics:

1. Plants of the new *Calibrachoa* are more mounding than and not as creeping as plants of the female parent selection.
2. Plants of the new *Calibrachoa* and the female parent selection differ in flower color.

The new *Calibrachoa* plant can be compared to plants of the male parent selection. Plants of the new *Calibrachoa* differ primarily from plants of the male parent selection in the following characteristics:

1. Plants of the new *Calibrachoa* are more mounding than and not as upright as plants of the male parent selection.
2. Plants of the new *Calibrachoa* and the male parent selection differ in flower color.

Plants of the new *Calibrachoa* can be compared to plants of the *Calibrachoa* sp. 'USCALI411-7', disclosed in U.S. Plant Pat. No. 19,492. In side-by-side comparisons conducted in Bonsall, Calif., plants of the new *Calibrachoa* differed primarily from plants of 'USCALI411-7' in flower color as plants of 'USCALI411-7' had orange-colored flowers.

Plants of the new *Calibrachoa* can be compared to plants of the *Calibrachoa* sp. 'USCALI413-8', disclosed in U.S. Plant Pat. No. 19,843. In side-by-side comparisons conducted in Bonsall, Calif., plants of the new *Calibrachoa* differed primarily from plants of 'USCALI413-8' in flower color as plants of 'USCALI413-8' had orange-colored flowers with red-colored centers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL09301' grown in a container.

The photograph at the top of the sheet is a close-up view of a typical flowering plant of 'USCAL09301'.

DETAILED BOTANICAL DESCRIPTION

The aforementioned photographs and following observations, measurements and values describe plants grown during the late autumn in one-gallon containers in a polyethylene-covered greenhouse in Bonsall, Calif. During the production of the plants, day temperatures ranged from 21° C. to 38° C., night temperatures averaged 21° C. and light levels ranged from 7,000 to 10,000 foot-candles. Plants were pinched one time and were 53 days old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL09301'.

Parentage:

- *Female, or seed, parent*.—Proprietary seedling selection of *Calibrachoa* sp. identified as code name 10CJ04-03, not patented.
- *Male, or pollen, parent*.—Proprietary seedling selection of *Calibrachoa* sp. identified as code number 10CJ70-02, not patented.

Propagation:

- *Type*.—By terminal cuttings.
- *Time to initiate roots, summer*.—About four days at temperatures ranging from 16° C. to 29° C.
- *Time to initiate roots, winter*.—About six days at temperatures ranging from 16° C. to 21° C.
- *Time to produce a rooted plant, summer*.—About 22 days at temperatures ranging from 16° C. to 29° C.
- *Time to produce a rooted plant, winter*.—About 25 days at temperatures ranging from 16° C. to 21° C.
- *Root description*.—Medium in thickness, fibrous; white in color.
- *Rooting habit*.—Freely branching; medium density.

Plant description:

- *Plant and growth habit*.—Upright, outwardly spreading to trailing and mounding plant habit; freely branching habit with about seven to eight primary lateral branches each with multiple secondary branches; pinching enhances branching; dense and bushy appearance; vigorous growth habit.
- *Plant height*.—About 18.8 cm.
- *Plant diameter*.—About 46 cm.

Lateral branch description:

- *Length*.—About 28 cm.
- *Diameter*.—About 2 mm.
- *Internode length*.—About 2.4 cm.
- *Strength*.—Strong.
- *Aspect*.—Initially upright to outwardly spreading to trailing.
- *Texture*.—Pubescent.
- *Color*.—Close to 144A.

Foliage description:

- *Arrangement*.—Before flowering, alternate; after flowering, opposite; leaves simple.
- *Length*.—About 4.4 cm.
- *Width*.—About 1.6 cm.
- *Shape*.—Elliptical.
- *Apex*.—Rounded.
- *Base*.—Attenuate.
- *Margin*.—Entire.
- *Texture, upper and lower surfaces*.—Pubescent; minute.
- *Venation pattern*.—Pinnate; arcuate to reticulate.
- *Color*.—Developing leaves, upper surface: Close to 144A. Developing leaves, lower surface: Close to 139C. Fully expanded leaves, upper surface: Close to 147A; venation, close to 147B. Fully expanded leaves, lower surface: Close to N138B; venation, close to 147C.
- *Petiole*.—Length: About 3 mm. Diameter: About 2 mm. Texture, upper and lower surfaces: Scattered pubescence. Color, upper and lower surfaces: Close to 146C.

Flower description:

- *Flower type and flowering habit*.—Single salverform flowers arising from leaf axils; freely flowering habit with usually about 20 to 21 flowers developing per lateral branch and about 200 flowers per plant; flowers face upright to outwardly.
- *Fragrance*.—None detected.
- *Natural flowering season*.—Early flowering habit, plants of the new *Calibrachoa* begin flowering about five weeks after planting; plants flower continuously from spring though the autumn in Southern California.
- *Flower longevity*.—Individual flowers last about three to four days on the plant; flowers persistent.
- *Flower buds*.—Length: About 2.2 cm. Diameter: About 6 mm. Shape: Elongated oblong. Color: Close to 1D.
- *Flower diameter*.—About 3.2 cm by 3.4 cm.
- *Flower length (height)*.—About 2.5 cm.
- *Flower throat diameter*.—About 6 mm by 9 mm.
- *Flower tube length*.—About 1.8 cm.
- *Flower tube diameter, base*.—About 2 mm.
- *Corolla*.—Arrangement: Five fused petals opening into a flared trumpet. Petal lobe length (from throat): About 1.3 cm. Petal lobe width: About 1.7 cm. Petal shape: Obovate. Petal apex: Rounded. Petal margin: Entire. Petal texture, upper and lower surfaces: Smooth, glabrous; velvety. Throat texture: Smooth, glabrous. Tube texture: Pubescent; minute. Color: Petal lobe, when opening, upper surface: Close to 3B. Petal lobe, when opening, lower surface: Close to 4C. Petal lobe, fully opened, upper surface: Close to 162B; towards the throat, ring around throat, close to 166A; venation, close to 176A to 176B and 183B to 183C; with development, ring color becomes more prominent and closer to 183A and center of petal lobe, closer to 183C to 183D. Petal lobe, fully opened, lower surface: Close to 161C; venation, close to 177A. Throat: Close to 161B; venation, close to 183B. Tube: Close to 160A; venation, close to 177A.

*Calyx*.—Arrangement: One star-shaped calyx tube with five sepals fused towards the base and arranged in a single whorl. Sepal length: About 1.5 cm. Sepal width: About 3 mm. Sepal shape: Lanceolate. Sepal apex: Rounded. Sepal margin: Entire. Sepal texture, upper and lower surfaces: Pubescent; minute. Color, upper and lower surfaces: Close to 146A.

*Peduncles*.—Length: About 2.6 cm. Diameter: About 1 mm. Angle: About 45° to 60° from stem axis. Strength: Strong. Texture: Pubescent; minute. Color: Close to 146D.

*Reproductive organs*.—Stamens: Quantity: Five per flower. Filament length: About 9 mm. Filament color: Close to 145C. Anther length: About 1 mm. Anther shape: Round. Anther color: Close to 10A. Pollen amount: Scarce. Pollen color: Close to 7B. Pistils: Quantity: One per flower. Pistil length: About 1 cm. Style length: About 7 mm. Style color: Close to 145D. Stigma shape: Round. Stigma color: Close to 146A. Ovary color: Close to 146B. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL09301' as illustrated and described.

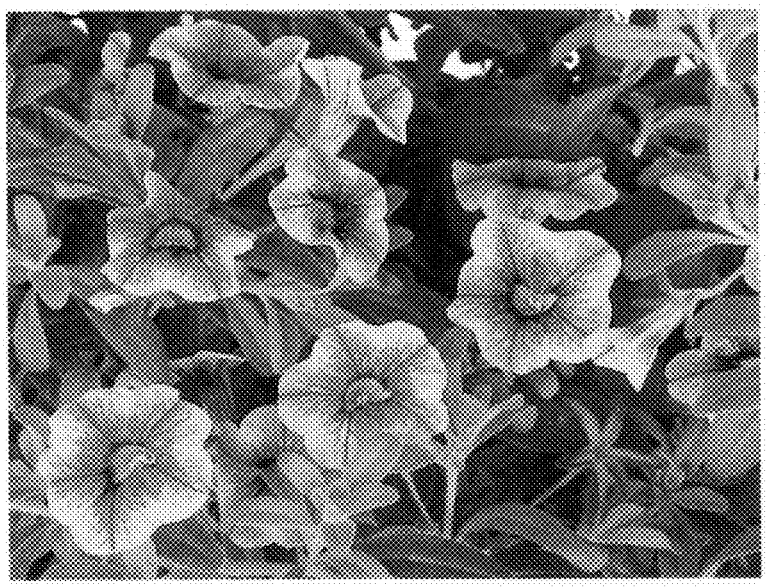
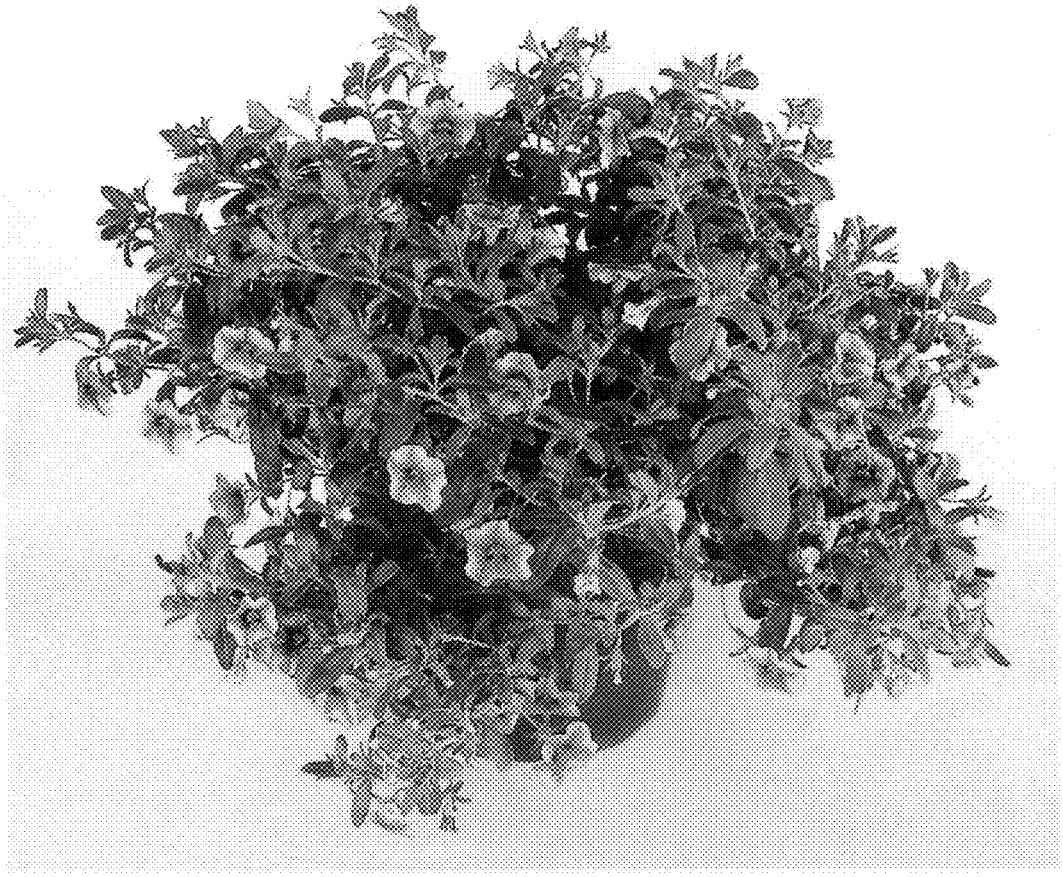

* * * * *